United States Patent
Feldman et al.

(10) Patent No.: US 6,245,132 B1
(45) Date of Patent: Jun. 12, 2001

(54) AIR FILTER WITH COMBINED ENHANCED COLLECTION EFFICIENCY AND SURFACE STERILIZATION

(75) Inventors: Paul L. Feldman, Sykesville; Dennis J. Helfritch, Baltimore, both of MD (US)

(73) Assignee: Environmental Elements Corp., Baltimore, MD (US)

( * ) Notice: Subject to any disclaimer, the term of this patent is extended or adjusted under 35 U.S.C. 154(b) by 0 days.

(21) Appl. No.: 09/633,883

(22) Filed: Aug. 7, 2000

Related U.S. Application Data

(62) Division of application No. 09/273,350, filed on Mar. 22, 1999.

(51) Int. Cl.⁷ ...................................................... B03C 3/74
(52) U.S. Cl. ................................ 96/28; 96/223; 422/121; 422/186.29
(58) Field of Search .................................... 95/59, 68, 74, 95/81, 278; 96/15, 16, 28, 223, 225, FOR 175; 422/186.29, 22, 121

(56) References Cited

U.S. PATENT DOCUMENTS

| | | | |
|---|---|---|---|
| 3,215,616 | 11/1965 | Spielman | 96/223 X |
| 3,739,554 | 6/1973 | Whetten et al. | 96/54 |
| 3,816,980 | 6/1974 | Schwab | 96/54 |
| 3,910,778 | 10/1975 | Shahgholi et al. | 96/16 |
| 4,205,969 | 6/1980 | Matsumoto | 96/66 |
| 4,376,642 | 3/1983 | Verity | 96/223 X |
| 4,406,672 | 9/1983 | Berz | 95/68 |
| 4,707,167 | 11/1987 | Saito et al. | 96/225 |
| 4,737,169 | 4/1988 | Bossard | 96/58 |
| 4,850,268 | 7/1989 | Saito et al. | 96/225 X |
| 4,976,749 | 12/1990 | Adamski et al. | 95/63 |
| 5,364,458 | 11/1994 | Burnett et al. | 96/55 |
| 5,403,383 | 4/1995 | Jaisinghani | 95/69 |
| 5,405,434 | 4/1995 | Inculet | 96/54 |
| 5,474,599 | 12/1995 | Cheney et al. | 96/55 |
| 5,474,600 | 12/1995 | Volodina et al. | 96/223 X |
| 5,540,761 | 7/1996 | Yamamoto | 96/67 |
| 5,549,735 | 8/1996 | Coppom | 96/63 |
| 5,573,577 | 11/1996 | Joannou | 96/66 |
| 5,593,476 | 1/1997 | Coppom | 95/78 |
| 5,632,954 | 5/1997 | Coellner | 96/225 X |
| 5,655,210 | 8/1997 | Gregoire et al. | 96/15 X |
| 5,759,239 | 6/1998 | Yu | 96/16 X |
| 5,814,135 | 9/1998 | Weinberg | 96/223 X |
| 5,938,823 | 8/1999 | Condit et al. | 96/225 X |
| 5,993,738 | 11/1999 | Goswani | 96/16 X |

*Primary Examiner*—Richard L. Chiesa
(74) *Attorney, Agent, or Firm*—Rosenberg, Klein & Lee

(57) ABSTRACT

Electrically enhanced filter, includes a filter element, a pair of electrodes sandwiching the filter element, a DC, AC, pulse, or RF power supply coupled to the electrode to create an electrostatic field across the filter element and to produce attracting forces between micro-organisms contained in the air and the filter element, and a power supply creating a sterilizing electrical field, which may be either an RF, DC, pulse, or AC power supply coupled to the electrodes and creating discharging or non-discharging voltages on the filter element to destruct the micro-organisms at and in the vicinity of the filter element.

7 Claims, 7 Drawing Sheets

Figure 1:
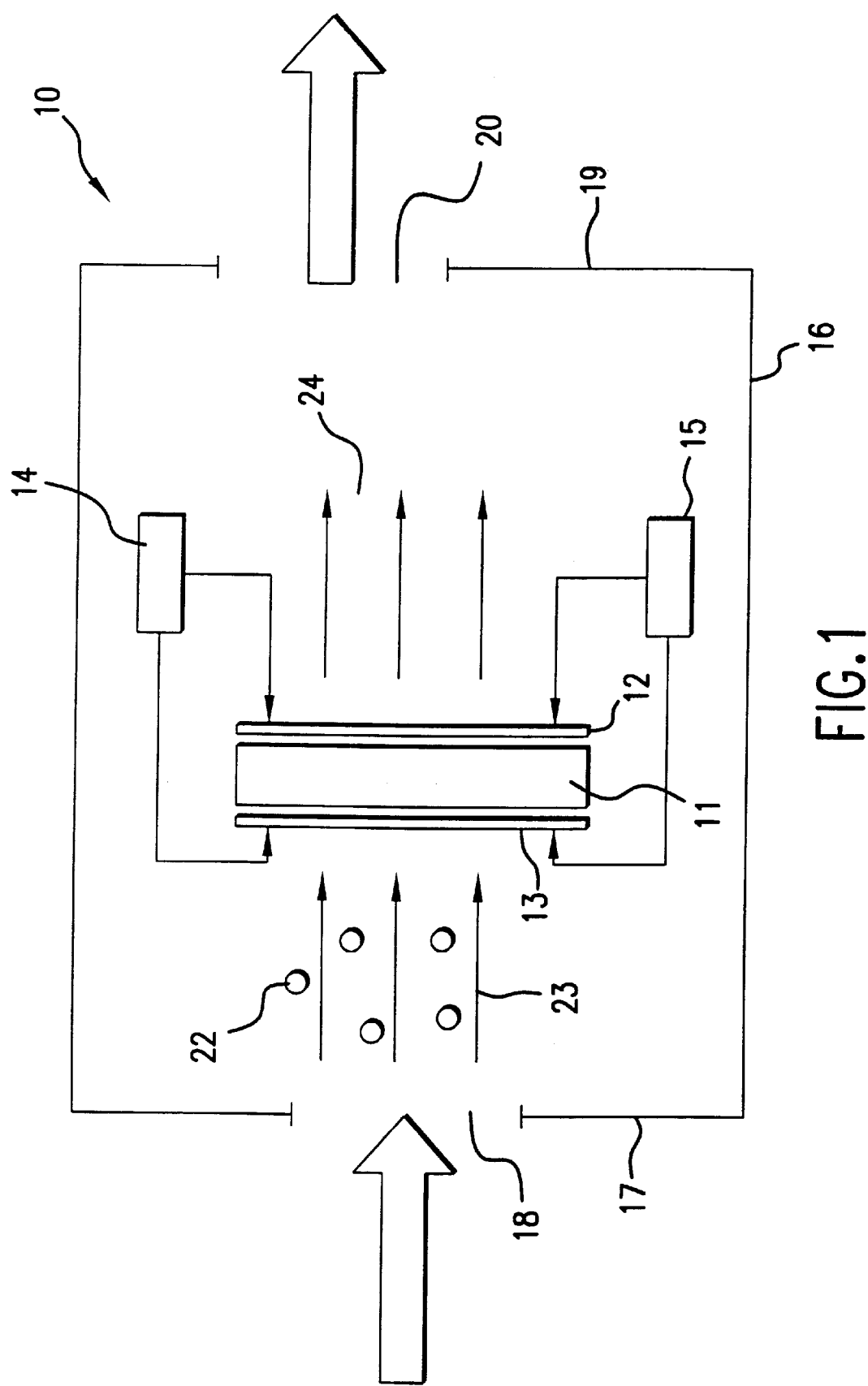

TABLE OF CELL COUNTS  
FIELD HEIGHT 0.5 INCHES

| EXPERIMENT NUMBER | FIELD TYPE | VOLTAGE kV | FIELD STRENGTH kV/INCH | ADDITIONAL DILUTION | EXPOSURE TIME MINUTES | CELL GROWTH RESULTS COLONY COUNT |
|---|---|---|---|---|---|---|
| 3B-C | -dc corona pins | 10.25 | 20.5 | 20 ml | 15 | 0 |
| 6A | ac corona pins | 6.43 | 12.86 | 0 ml | 15 | 2 |
| 1B-C | -dc flat | 10 | 20 | 10 ml | 240 | 4 |
| 4B | -dc corona dry | 10 | 20 | 0 ml | 15 | 6 |
| 6A-C | ac corona pins | 6.39 | 12.78 | 20 ml | 15 | 9 |
| 1E-C | -dc flat | 12 | 24 | 10 ml | 120 | 11 |
| 1A-C | -dc flat | 12 | 24 | 20 ml | 60 | 22 |
| 5A-C | ac flat | 6.5 | 13 | 20 ml | 45 | 26 |
| control | none | none | none | 20 ml | 0 | 28 |
| 3A | -dc corona pins | 10 | 20 | 0 ml | 1 | 50 |
| 1A | -dc flat | 12 | 24 | 0 ml | 60 | 60 |
| 3B | -dc corona pins | 10.25 | 20.5 | 0 ml | 15 | 100 |
| 1B | -dc flat | 10.75 | 21.5 | 0 ml | 240 | 100 |
| 2B | -dc pulsed flat | 25 | 50 | 0 ml | 60 | 100 |
| 4A | -dc corona dry | 10.75 | 21.5 | 0 ml | 2 | 200 |
| 5A | ac flat | 6.5 | 13 | 0 ml | 45 | lawn |
| 1C | -dc flat | 11.5 | 23 | 0 ml | 2 | lawn |
| 2A | -dc pulsed flat | 38 | 76 | 0 ml | 5 | lawn |
| control | none | none | none | 0 ml | 0 | lawn |

FIG.5

AIR FILTER WITH COMBINED ENHANCED COLLECTION EFFICIENCY AND SURFACE STERILIZATION

This application is a divisional of application Ser. No. 09/273,350 filed on Mar. 22, 1999 and which designated the U.S.

BACKGROUND OF THE INVENTION

1. Field of the Invention

The present invention relates to air filters, and more particularly to the air filter having improved capture efficiency of micro-organisms contained in the air; and even more particularly, the present invention relates to an air filter having combined electrically enhanced filtration and surface discharge (plasma) or non-discharge sterilization for destruction of the captured micro-organisms.

2. Prior Art

The problem of purification and filtration of indoor air is an important one and cannot be over-estimated. Tuberculosis, legionella, sinusitis, allergies, bronchitis, asthma, and other health problems can be caused to the large extent by the indoor air pollution. Therefore, air filtration systems providing an adequate particle removal efficiency are constantly needed for purification of the indoor air.

Numerous air filters with electronically enhanced capturing capability have been described in the literature and are available in the commercial marketplace. In some of these systems, the improvement of a filter's capture efficiency is achieved through the application of electrostatic fields to a filter. For example, a high efficiency electronic air filter is disclosed in U.S. Pat. No. 5,573,577 in which pads of dielectric fibers are sandwiched between electrically charged ionizing elements, and grounded screens. The ionizing elements charge the dust particles passing through the filter and at the same time, polarize the fibrous filter pads. In this way, the charged particles are attracted and collected on the fibrous pads with improved efficiency.

As disclosed in U.S. Pat. No. 5,405,434, an electrostatic filter for purifying air in an HVAC system includes a pair of conductive filaments insulated from one another and disposed close together in a substantially parallel side-by-side relationship. Circuitry is provided for applying an electrical potential difference between two conductors. The strong electric fields cause the wire sets to attract fine airborne particulate matter in the vicinity of the filter mesh so that the mesh retains dirt, atmospheric ions, and other very fine particles. Such particles include pollen and bacteria borne by the air stream passing through the mesh which are removed from the air.

U.S. Pat. No. 5,593,476 describes a high efficiency air filtration apparatus utilizing a fibrous filter medium that is polarized by a high potential difference which exists between a pair of electrodes. The electrodes include an insulated electrode and an uninsulated electrode. A corona precharger is positioned upstream of the electrodes and filter. The corona precharger applies a charge to particles which are removed from the air flow system as they accumulate on the filter surfaces proximal to the insulated electrode.

Although filters are good candidates for removing submicron airborne particles (0.3 micrometer diameter particles are captured with efficiency greater than 99%), their capture efficiency however decreases rapidly for particle diameters below 0.3 microns. This is a major disadvantage of electrically enhanced high efficiency particulate air filters since these filters fail to effectively purify the indoor air from airborne micro-organisms hazardous to health. The filtration of bacteria and viruses from indoor air is hindered by two characteristics of the organism which are the extremely small size of the organisms and the ability of the organisms to propagate. The typical diameter of bacteria is a few micrometers, however, viruses can be 1/100th of this diameter. Therefore, it is not only difficult to capture airborne pathogens on the filter material due to their small dimension, but also the organisms that are captured by the filter may propagate on the filter surface and migrate through the filter. These combined factors necessitate frequent filter changes. The control of airborne pathogens in an indoor environment is especially acute due to the fact that a major, if not predominant source of airborne micro-organisms results from entrainment of colonies that have grown on the filter.

In external environments such as outdoor air, the micro-organisms die as a result of sunlight, temperature extremes, and dehydration. However, for indoor conditions, the range of temperatures is relatively narrow and the air is shielded from direct sunlight. Further indoor air may be humidified, thus aiding in propagation of the organisms. Relative to outdoor air, the quality of indoor air can be 20–70 times worse. An example of the seriousness of biological contamination in indoor air is Legionnaires disease. The legionella bacteria were first discovered in 1976 as a result of the Legionnaires disease outbreak in Philadelphia that caused 200 cases of this disease. Legionella was found to be the cause of a similar outbreak the previous year at the same hotel as well as a series of mysterious epidemics going back 50 years.

Another example, tuberculosis, is spread via the air through inhalation. *Microbacterium tuberculosis* is carried in airborne particles known as droplet nuclei that are generated when persons with pulmonary or laryngeal tuberculosis sneeze, cough, speak, expectorate, or exhale. The droplet nuclei are so small (1–5 micrometers) that they can be suspended indefinitely in the air and be spread throughout a facility by an HVAC system. The probability that a susceptible person becomes infected with microbacterium tuberculosis depends primarily upon the concentration of infectious droplet nuclei in the air and the exposure duration. Unlike other airborne diseases, which require large aerosolized colonies of bacteria to produce an infection, one tuberculosis bacillus is enough to infect humans.

None of the known filter systems, even those with electrically enhanced capture efficiency appear to prevent micro-organisms propagation and entrainment into the indoor air from the filter.

It is, therefore, clear that the problem of airborne pathogens in indoor environments has not been solved by the electrically enhanced filters which are known to those skilled in the art. Therefore, a new, improved air filter is needed which would not only has an increased capturing efficiency, but also provides a biocontaminant control of the indoor environment by impeding propagation of the pathogens on the filter surface and preventing re-entrainment of the organisms into the air from the filter.

SUMMARY OF THE INVENTION

It is therefore an object of the present invention to provide an air filter capable of capturing even the smallest airborne organisms and destroying the organisms thus captured.

It is another object of the present invention to provide an air filter having combined electrostatically enhanced filtration performance and high sterilization efficiency.

It is still a further object of the present invention to provide an effective indoor air biocontaminant control by collecting airborne pathogens on a filter and killing them at the place of deposition and in vicinity thereof by glow discharge or non-discharge fields.

The present invention may find utility in any air handling system, such as HVACs, or other systems which displaces and/or distributes air in a relatively closed environment.

In accordance with the present invention, an electrically enhanced filter includes a filter media towards which air stream laden with micro-organisms and other particulates is directed. The filter includes a pair of electrodes sandwiching the filter media therebetween having one or two power supplies coupled to these electrodes. One power supply may be a DC power supply creating an electrostatic field applied across the filter media between the electrodes and produces attractive forces between the micro-organisms (as well as other particulates in the air stream) and the filter media to enhance filtration efficiency of the filter. The AC or DC power supply is coupled between the first and second electrodes and operate constantly without interruption.

Where a second power supply is applied, such may be RF, DC, pulse, or AC power supply which is intermittently operationally coupled to the electrodes for applying intermittent RF electrical field across the filter media creating periodic uniform gas discharge to destroy the micro-organisms collected by the filter media and in the vicinity thereof.

It is noted that instead of the RF power supply, a non-discharging electric field may be used which would create a strong non-discharge "flat" field causing a significant reduction in the number of active micro-organisms collected in the filter media.

The filter media, preferably is formed of a dielectric material which may be a spun fabric dielectric, glass fibers, polypropylene or polyester, or other like material composition.

Both electrodes are porous electrodes, which allow an airstream to pass therethrough. Preferably, the first electrode includes a plurality of electrically conductive (uninsulated) wires interconnected in a substantially parallel arrangement structurally held together by an insulated frame. Another electrode includes a plurality of insulated wires interconnected in a mesh type arrangement which is also structurally coupled by an insulated frame.

The power supply is intermittently coupled between the electrodes for predetermined discharge time sufficient to destroy the micro-organism. For example, exposure times on the order of minutes are applied for killing a wide range of micro-organisms.

Viewing the subject system from another aspect, the present invention teaches a method of filtering air from airborne micro-organisms (and other particulates) which includes directing airstream laden with micro-organisms (and other particulates) towards filtering medium.

A second step applies permanent electrostatic fields across the filtering medium, thereby enhancing capturing efficiency of the filtering media. In one embodiment, the invention intermittently applies a discharging electrical field across the filtering media, which generates periodic uniform gas discharge on the surface of the filtering media, or applies a strong non-discharging electrical field, thereby destroying the micro-organisms collected at and in the vicinity of the filtering media.

In a concluding step, airstream purified from the micro-organisms (and other particulates) is directed from the filtering media.

These and other novel features and advantages of this invention will be fully understood from the following detailed description and the accompanying Drawings.

BRIEF DESCRIPTION OF THE DRAWINGS

FIG. 1 shows schematically a filter of the present invention;

FIG. 2 is a perspective view showing filter medium-electrodes arrangement in the filter of the present invention;

FIG. 3A shows the structure of the downstream electrode of the present invention;

FIG. 3B shows the structure of the upstream electrode of the present invention;

FIG. 4 shows schematically an experimental set-up for testing the filter efficiency of the filter of the present invention;

FIG. 5 presents a Data Table collected during tests;

FIG. 6 shows schematically the electromicrobicide test array; and,

FIG. 7 is a diagram showing the percent survival of *E. coli* cells for various lengths of exposure to a strong non-discharge DC electric field.

DETAILED DESCRIPTION OF THE PREFERRED EMBODIMENT

Referring to FIG. 1, the filter system 10 of the present invention includes filter medium 11, a pair of electrodes 12 and 13 sandwiching the filter medium 11 therebetween, and power sources 14 and 15 electrically coupled to the electrodes 12 and 13. The entire arrangement is housed within a filter housing 16, the wall 17 of which has an input 18, and a wall 19 of which has an output 20.

An airstream 23 laden with particulates, such as dust, inorganic particles, and/or living micro-organisms 22, may be directed by a conventional electrically powered blower (not shown) towards through the input 18 of the housing 16 towards the filter medium-electrodes arrangement. After filtration, the purified air stream 24 substantially devoid of airborne particulates is directed from the filter medium to the output 20 and is supplied to a facility where it is intended to be used.

Electrode 12 is located downstream of the airstream, while the electrode 13 is positioned upstream of the airstream. As shown in FIGS. 2, 3A and 3B, electrode 13 is a wire mesh formed of a conductive electrode core (copper or other electrically conductive metal), which is completely covered or coated with insulation. The insulation may include, for example, any material having a dielectric constant greater than that of the electrode, and materials, such as glass fiber, silicon elastomers, or like material having a high dielectric constant. As best shown in FIGS. 2 and 3B, electrode 13 has an insulating frame 25 surrounding the wire mesh of electrode 13.

Electrode 13 may be insulated by any method known to those skilled in the art, which may include, for example, dipping or spraying simultaneously, extruding or injection molding an insulator with the wire, and/or joining together injection molded insulator sections around a wire.

Electrode 12, best shown in FIG. 3A, is formed of uninsulated wires which are arranged in parallel to each other and framed by insulated frame 26.

Filter medium 11 may be a commercially available thermostat filter made of manmade materials such as polypropylene, or polyester, or any other fibrous filter element, which may be flat or somehow else shaped to increase the surface area thereof. To simplify the discussion, filter medium 11, for purposes of example, is a rectangular flat piece of dielectric fibrous material with dimensions of 1'×1'. The filter medium 11 is sandwiched between the electrode 13 and the electrode 12 which are opposedly charged with DC power source 14 and RF power source 15, respectively, both coupled to the electrodes 12 and 13.

The DC power source 14 charges the insulated electrode 13, for instance, with a negative charge, while the uninsulated electrode 12 is charged with a positive charge, thereby creating an electrostatic field applied across the filter medium 11. The field applied to the electrodes may be as high as 20 kilovolt per inch. The applied field induces a polarization state along the respective lengths of individual fibers of the filter medium 11.

In operation, a blower (not shown) moves particle laden incoming air 23 through the input 18 and through the pores 27 of the back electrode 13 to the filter medium 11.

Therefore, the air passing through the filter medium 11 leaves the particulates, including micro-organisms 22, on the filter medium 11. Electrostatic fields applied across the filter medium 11 result in optimized collection efficiency which may be as high as approximately 99% for a one micron particle. Either one of the electrodes may be insulated so as to inhibit spark-over. Any charge may be applied to the electrodes 12 and 13 so long as they are charged by opposite sign.

The filter medium 11 captures inorganic particulates and living micro-organism 22 which may propagate through the filter surface. The micro-organisms 22 may grow colonies on the filter and further may re-entrain into the airstream supplied to facilities, thereby biologically contaminating the indoor environment. In order to impede contamination of the indoor air by micro-organisms collected at and captured in the vicinity of the filter medium, the filter medium 11 is sterilized in order to destroy the micro-organisms which are deposited at and retained in the vicinity of the filter medium 11. The sterilization may be performed either by subjecting the microorganisms to glow discharge or to non-discharge strong electrical fields.

For creating a discharge, the filter 10 of the present invention may be provided with RF power supply 15 or pulse, AC or DC power supplies which, being coupled to the electrodes 12 and 13, may generate a plasma sheet on the surfaces of the filter medium 11 when an AC or pulse power is applied. The electrodes 12 and 13, positioned on both sides of the dielectric filter sheet 11 and energized with the RF power source 15 constitutes a uniform glow discharge plasma reactor. When the dielectric filter medium 11 captures bacteria and viruses, the plasma produced by the periodic energization of the electrodes 12 and 13 sterilizes the filter medium 11 and kills the captured organisms.

Figure 2:
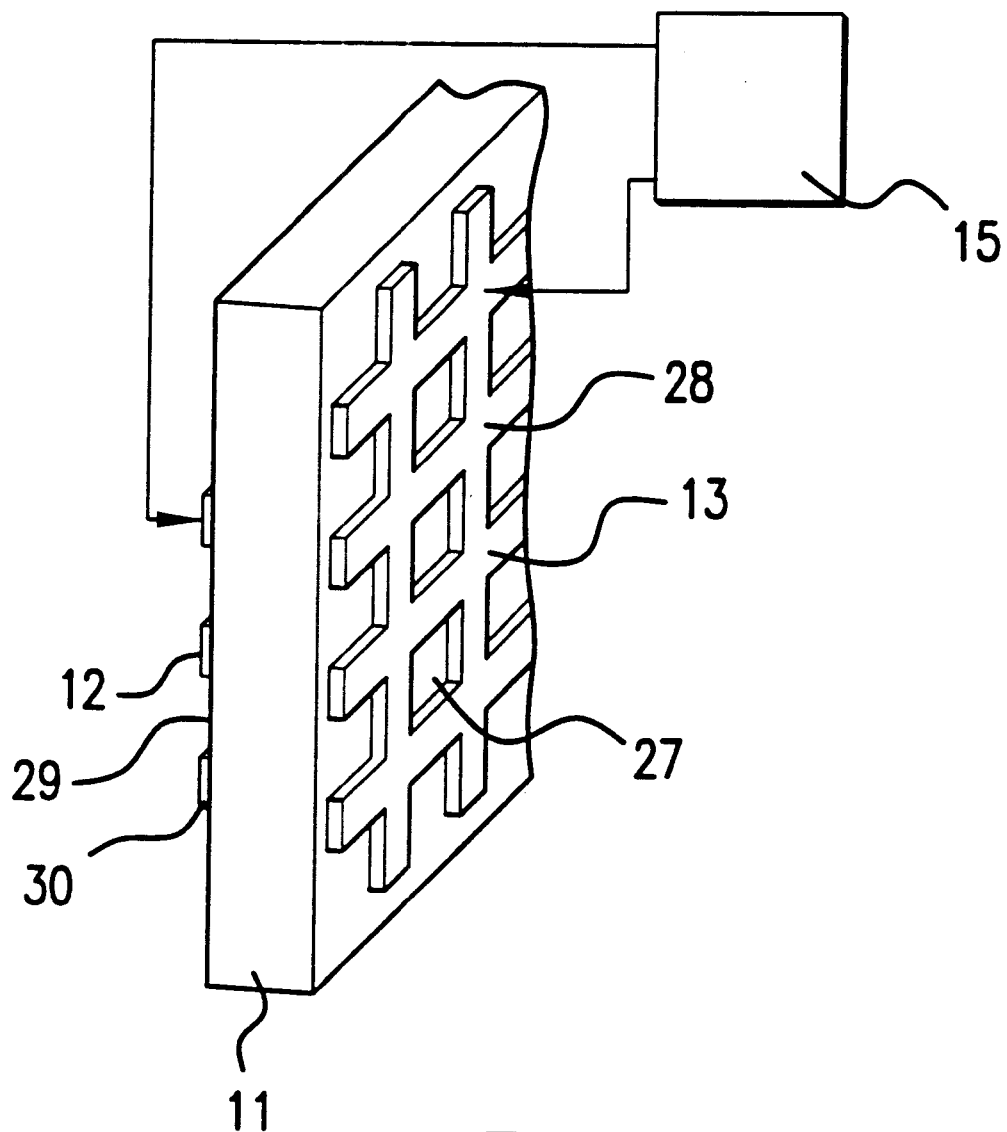
Figure 3A:
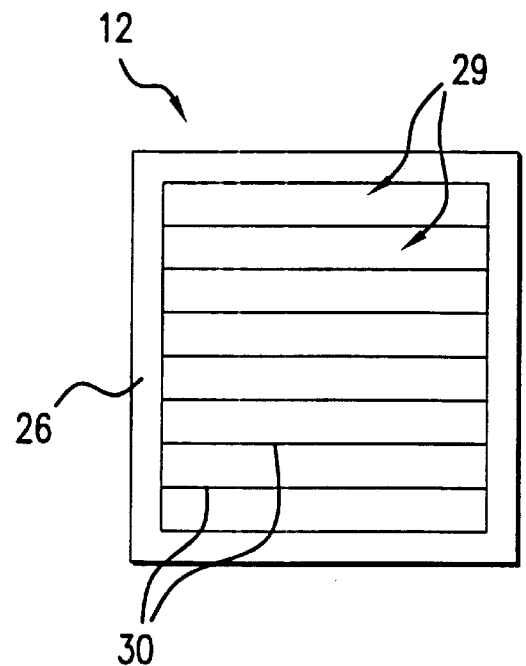
Figure 3B:
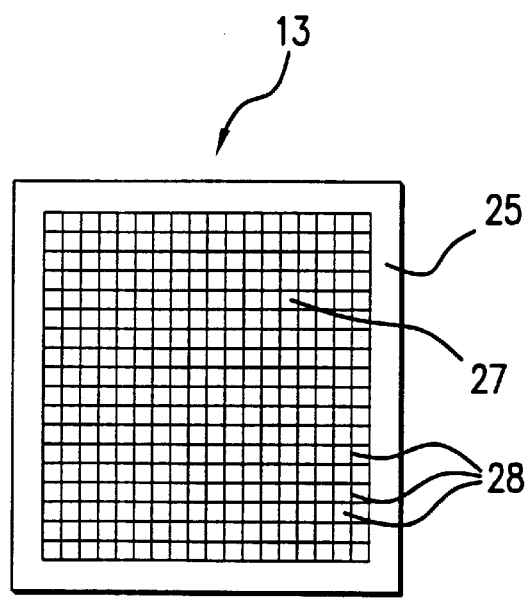

By permanently applying a DC, AC, RF, or pulse voltage to the electrodes 12 and 13 below the discharge onset (thereby enhancing particle capture across the filter medium) and by periodically applying voltages from the power source 15 (thereby sterilizing the filter medium 11), the filter 10 of the present invention provides a desired substantially complete purification of the indoor air. In overall flow, the air is directed from the filter medium 11 through spaces 29 of the electrode 12, shown in FIGS. 2 and 3, existing between wires 30 of the electrode 12, to the output 20 of the filter housing 16.

As previously discussed, in order to create a non-discharge field, power source 15 shown in FIG. 1 may be either a DC power source, AC power source, or pulsed power supply.

The sterilization of surfaces of the filter medium 11 through exposure to low temperature gas discharges or to strong non-discharge electrical fields, as above presented, has been demonstrated to be very effective. The combination of electrostatic filter enhancement and plasma filter sterilization applied to a conventional air filter results in an effective capture and destruction device for even the smallest organisms.

Figure 4:
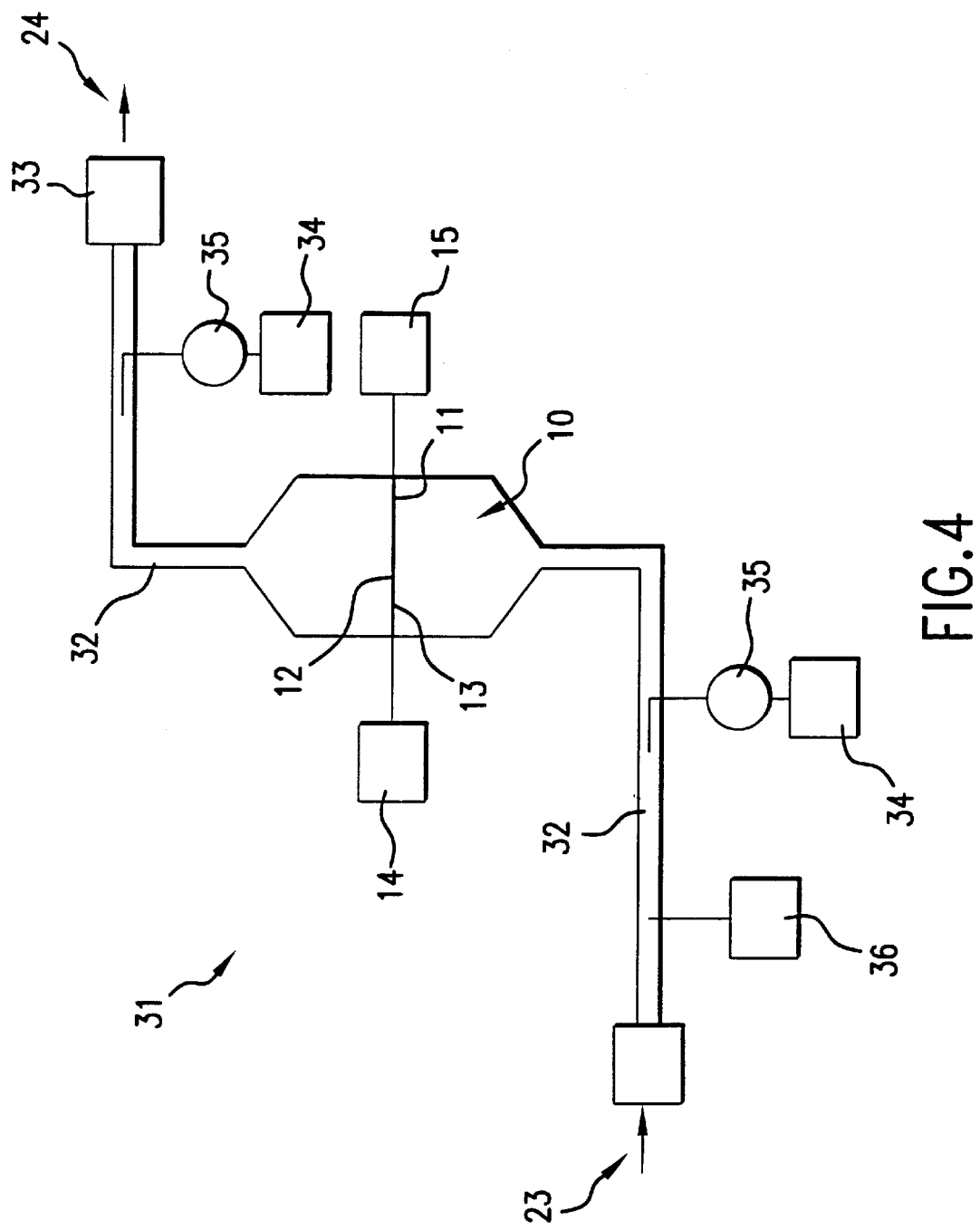
Figure 6:
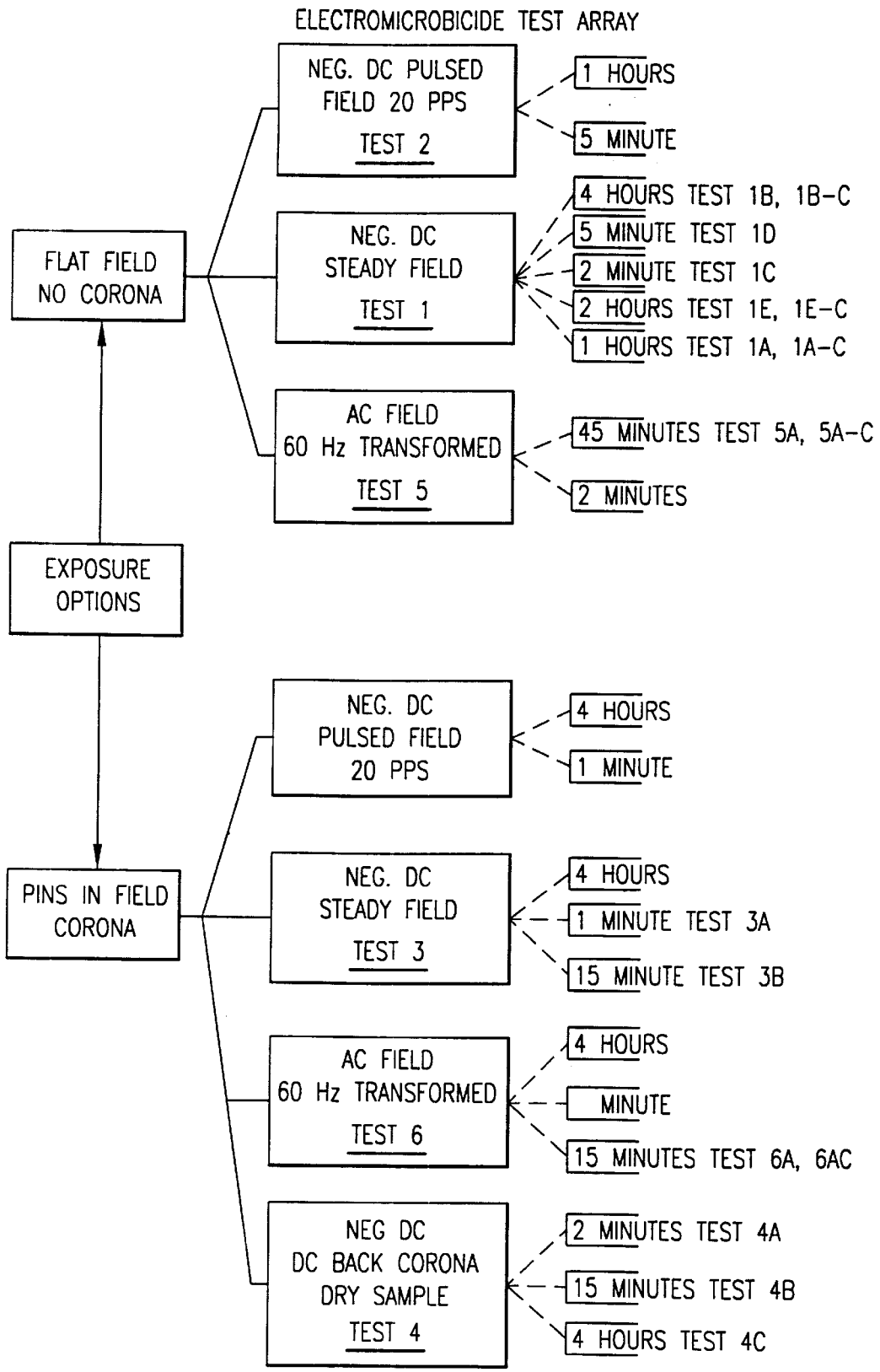
Figure 7:
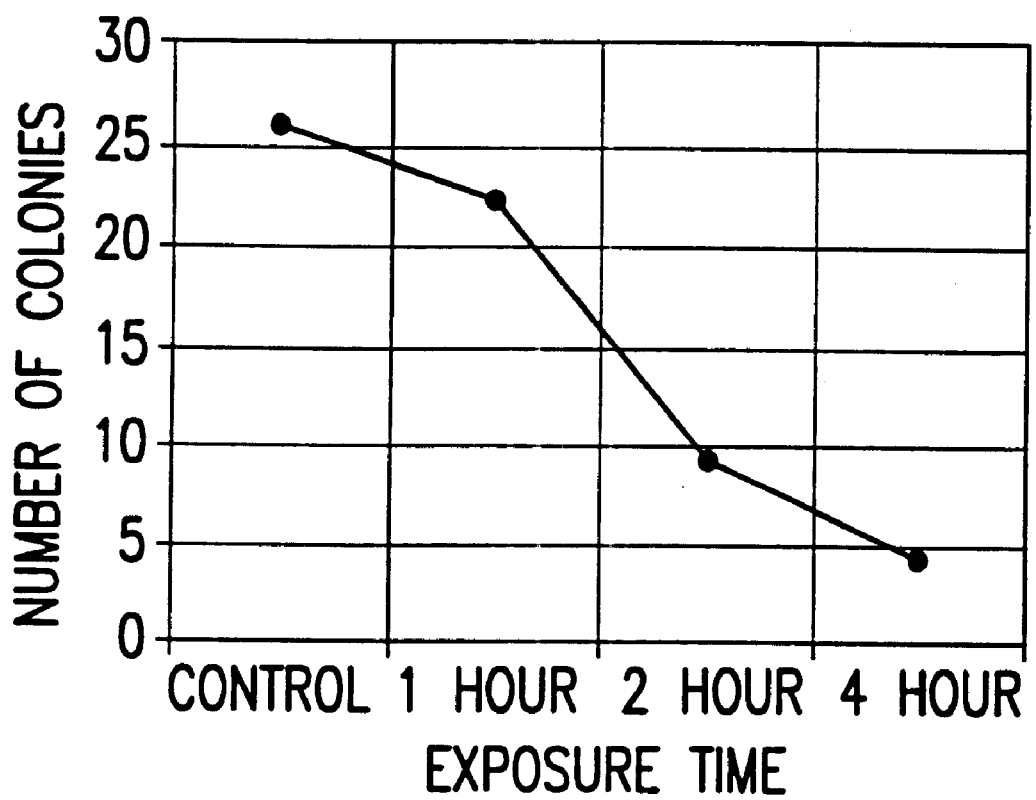

In order to demonstrate the effectiveness of electric field biological decontamination of indoor air, an experimental set-up 31, shown in FIG. 4, was prepared. The experimental set-up 31 includes an electro filter 10, a room air intake duct 32 leading to the electro filter 10. A DC power supply 14 provides a continuous electric field for filtration enhancement, and a power supply 15 provides plasma sterilization. The air flow passes through the filter 10 and is subsequently exhausted to an external environment through a fan 33. Micro-organisms 22 are introduced upstream of the filter 10 by an atomization technique. The micro-organisms penetrating the filter medium 11 of the filter 10 were measured by means of pump and flow control devices 34, and filters 35 for taking samples in upstream and downstream portions of the duct 32 provided for this purpose. The organism capture and destruction is determined by rinsing the filters 35 with subsequent culturing of the rinse solution to determine the amount of organisms.

The experiments were focused on two classes of micro-organisms— bacteria and virus. The reasons for inclusion in the study is their ability to provide detection of sub-lethal stress and the ability to produce endospores. With regard to sub-lethal stress, bacteria are composed of a cell wall, which provides protection from the environment. They include a selectively permeable phospholipid bilayer membrane, and a cytoplasm. Within the cytoplasm is a nucleic acid DNA, referred to as the nucleoid.

Based upon cell wall structure, bacteria are divided into two major groups, Gram positive and Gram negative cells. One Gram negative model organism, *E. coli* JM105/pGFP-sigma, has been cloned to carry a green fluorescent protein, so that when stressed, it fluoresces bright green upon exposure to UV or blue light, thereby providing detection of sub-lethal stress. With regard to the ability of bacteria to produce endospores, the microbe *S. Aureus* will form endospores that cannot be destroyed easily in response to environmental stress. The spores remain capable of germination into the vegetative cells for many years.

In the experimental arrangement shown in FIG. 4, the micro-organisms were nebulized into aerosols, and introduced by a nebulizer 36 into the duct 32 upstream of the electric filter 10. The filter efficiency was measured by the use of the downstream compression device 35 and the filtration rate was measured by the cultivation of the cells or micro-organisms taken from the filter medium 11.

As discussed in previous paragraphs, the filter 10 was tested with a bacteria and a virus. These organisms were exposed to the electrical field for periods of operation of up to 15 minutes. The sample passed through a densely packed fibrous filter at very low velocity such that particles as small as 0.01 micrometers diffused to the fibers. The micro-organisms were then removed from the filter by direct immersion in a known volume of buffer, and plate counts were made.

It was found that ten minutes of plasma exposure destroyed 99.99% of either microorganism. The application of a DC electric field decreased the penetration of *S. Aureus* bacteria through polypropylene by a factor of 10.

A second test program was designed to test the capability of three generic modes for producing the electric fields—DC, AC, and pulse DC power sources, to destroy microorganisms. The negative DC power supply (a hippotronic capacitive voltage multiplier) provided a variable voltage between 500 and 10,000 volts and created a field strength between 1,000 and 20,000 volts per inch.

A 60 Hz AC power supply (constructed from a variac and an oil furnace transformer with an 81:1 ratio) provided variable voltage between 1,500 and 10,000 volts to create a field strength between 2,500 and 20,000 volts per inch.

A small scale pulse power supply (consisted of hippotronic DC supply connected to a variable frequency pulsing device) was built to provide a pulsing negative DC supply of 20 to 100 pulses per second at 2,000 to 10,000 volts.

The following technique was used to expose *E. coli* to a strong electric field:

1. Arrange field plates in parallel configuration such that even field strength is obtained. This is done by using spacers of the appropriate distance on either side of the field plates.
2. Connect negative DC to the top plate and ground the bottom plate to massive earth ground.
3. Decontaminate the chamber plates by swabbing with alcohol.
4. Prepare small (1.5 inches×1.5 inches) squares of fiberglass cloth by heating in an oven to 350 F. for 8 hours. This provides uncontaminated filter media for placing the bacteria in the chamber.
5. Place the uncontaminated square of filter media in the chamber.
6. Place another uncontaminated filter square in the control dish.
7. Dose each of the filter cloths with 0.1 microliters of diluted *E-coli* bacteria using a pipette. Select a clean pipette tip for each dosing of the filter media. *E-coli* was previously diluted at $1{:}10^7$.

8. When dry media is required, measure the resistance of the cloth and then compare to the resistance of the dosed area. When the dosed area is the same resistance as the dry cloth begin the electrification.

9. Activate the chamber, using the appropriate power supply for the specific test, for the test time period, recording the voltage and current readings periodically, as shown in Table 1 of FIG. 5.

10. Record data.

11. Remove the fiberglass cloth from the test chamber and press into the growth agar at numerous places taking care not to tear the growth media.

12. Remove the fiberglass cloth from the control Petri dish and press into the growth media at numerous places taking care not to tear the growth media.

13. Culture the agar dishes in a warm oven, 80 to 90 degrees F., until growth is complete.

14. Obtain results of bacteria colonization—a milky white indicates growth. Individual colonies will be the size of a pinhead to an eraser head in diameter.

In this portion of the experiment, humidity and temperature of the chamber of the filter was varied, to measure the sensitivity to environmental conditions on the ability to inactivate micro-organisms. The samples were collected from the filter at intervals of several hours for determining viability in order to enable the delineation of the destruction rate.

For Modified Procedure for reducing colonization counts step numbers 11–12 are modified as follows:

After activation of the electric field, place the contaminated cloth in a vessel with 20 ml of sterile $H_2O$; agitate the vessel for 2 minutes, then draw of 0.1 microliters of the dilute solution. Dose the solution onto the agar dish and using a glass hockey puck; distribute the solution over the entire dish.

For Modified Procedure for placing filter media in the field, steps number 1–6 are modified as follows:

A special chamber is made to allow holding of a circular fiberglass 2.75 inches diameter filter media. The chamber has 2.5 inch diameter holes allowing the filter to be suspended exactly between the field plates. After the filter has been positioned, the media is dosed and the experiment carried out as usual. Control filters are only needed to block changing environmental conditions.

For the procedure described above, the field chamber was made from two 2¾"×2¾"×5⁄16" aluminum plates. The plates were drilled and tapped to allow attachment of high voltage cables to each. The plates were then spaced from one another using ¼" thick plexiglass sheets. The sheets were drilled with 2½" diameter holes to allow placement of the filter media.

Dosing of the filter media and extracting diluted *E-coli* was accomplished by using a calibrate pipette and pipette tips.

Distribution of the *E-coli* onto the growth media was done using sterilized bent glass rods made by bending glass stirring rods over a flame. The conformed glass rods were alcohol washed and flame sterilized.

Referring to FIG. 6, the experiment matrix shows the tests that were proposed to verify cell inactivation by electric field.

Exposure of *E-coli* cells to electric fields of both non-discharge and discharge, greatly reduces, and in the case of discharge fields completely inactivates the cells being tested. This is determined by counting the number of colonies that were cultured in the agar growth media. Table 1 presented in FIG. 5 summarizes the collected experiment data. In earlier tests the *E-coli* was not diluted after exposure and large quantities were incubated in all of the controls as well as some of the exposures. In tests with a −C designation the *E-coli* was diluted after exposure in order to obtain the cell inactivation efficiencies. DC fields were approximately 20 kV/inch; but slightly lower power levels were achieved with AC (around 13 Kv/inch). As expected, the pulsed field strengths were much higher, around 50 to 70 kV/inch. All pulsed fields were run at 20 pulses per second.

Table 1 is sorted, in order of increasing cell growth, therefore the most effective field properties are listed at the upper portion of Table 1.

The data clearly indicates that not only a corona discharge, but also a strong electric field causes a significant reduction in the number of active *E-coli* cells. It is noteworthy that using the non-corona fields, regardless of cell dilution, little evidence of cell inactivation occurred during the 1 min, 2 min, 5 min, 15 min, or 45 minute exposures. This suggests that there is a time/intensity effect to cell destruction for non-corona fields. In the subsequent one to three hours of exposure, the reduction in active cells is significant. The graph of the −DC field data shown in FIG. 7 illustrates this effect. The field strength used in the tests was the maximum attainable before sparking would occur.

Referring again to FIG. 7, which shows the percent survival of *E. coli* cells for various lengths of exposure to a 20 KV-inch electric field, specifically, *E. coli* JM105/PGFP-sigma cells were seeded at known concentration onto sterile Whatman filter paper. They were exposed to the field, washed, and plated asceptically onto agar plates. The plates were grown at ambient temperature for two days. Test samples were compared to unexposed control cells. All experiments were performed in duplicate. It was found that 100% kill of this *E. coli* was accomplished in less than 72 hours.

As discussed in previous paragraphs, the electrically enhanced filter having the high capturing efficiency and high micro-organism destruction efficiency (99%+) was developed and demonstrated. As the result of tests performed, it was concluded that a) living microorganisms can be deactivated using either a corona discharge or non-discharge strong electric fields, and b) corona discharge is not necessary to inactivate the microorganisms if a long enough exposure to a strong DC field is allowed.

The successful demonstration of the proposed concept and device allows extremely efficient micro-organisms control for indoor air. The electrically enhanced filter improves the collection of sub-micron organisms (and inorganic particles) by an order of magnitude over some prior art, and thus, is capable of controlling indoor air viruses, as well as bacterial pathogens. The commercial market for such a filter device clearly includes those areas that are traditionally highly susceptible to airborne pathogens, such as hospitals and other medical facilities. It can also include any other facility for which effective control of airborne pathogens would lead to the improved health of occupants such as schools and offices.

In addition, the device of the present invention provides improved fine particle control for any facility intended for micro-electronic fabrication. The proposed device can directly replace the high efficiency particulate air conventional filters without modifying the duct work or any other component of the HVAC system. It can be designed to use the same mounting hardware now used for high efficiency particulate air filters. Only a small electrical power supply and its control would be needed to be added to the system.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described. Certain features may be used independently of other features, and in certain cases, particular location of elements may be reversed or interposed, all without departing from the spirit or scope of the invention as defined in the appended Claims.

What is claimed is:

1. An electrically enhanced filter, comprising:

a filter medium;

first and second electrodes sandwiching said filter medium therebetween;

an air stream input directed towards said filter medium and laden with micro-organisms;

first means for attracting said micro-organisms towards said filter medium, said first means including a DC power supply coupled to said first and second electrodes, said DC power supply creating a continuous electrostatic field across said filter medium and producing attracting forces between said micro-organisms and said filter medium to thereby enhance filtration efficiency of said filter;

second means for sterilizing said filter medium to destroy said micro-organisms and impede unwanted propagation thereof, said second means including means for intermittently applying a sterilizing electrical field between said first and second electrodes concurrently with said electrostatic field, said intermittent sterilizing electrical field being of sufficient magnitude to generate a plasma sheet on surfaces of said filter medium; and an air stream output directed from said filter medium and substantially purified from said micro-organisms.

2. The filter of claim 1 where said means for intermittently applying a sterilizing electrical field includes a second DC power supply intermittently coupled to said first and second electrodes for a predetermined exposure time sufficient to destroy said micro-organisms.

3. The filter of claim 1, wherein said means for intermittently applying a sterilizing electrical field includes an AC power supply intermittently coupled to said first and second electrodes for a predetermined exposure time sufficient to destroy said micro-organisms.

4. The filter of claim 1 where said means for intermittently applying a sterilizing electrical field includes an RF power supply intermittently coupled to said first and second electrodes for a predetermined exposure time sufficient to destroy said micro-organisms.

5. The filter of claim 2 where said second DC power supply is a pulse power supply.

6. The filter of claim 1, wherein said second means includes a uniform glow discharge plasma reactor.

7. An electrically enhanced filter, comprising:

a filter medium;

first and second electrodes sandwiching said filter medium therebetween;

an air stream input directed towards said filter medium and laden with micro-organisms;

means for applying a continuous electrostatic field between said first and second electrodes to thereby enhance a capture efficiency of said filter medium;

means for intermittently applying a sterilizing electrical field between said first and second electrodes, said sterilizing electrical field being a non-discharging electrical field applied concurrently with said electrostatic field, said intermittent sterilizing means applying said non-discharging electrical field across said filter medium for a duration sufficient to have a sterilizing effect and thereby destroy said micro-organisms collected at said filter medium and in a vicinity thereof and further enhancing said capture efficiency of said filter medium; and, an air stream output directed from said filter medium and substantially purified from said micro-organisms.

* * * * *